United States Patent
Scheele et al.

(10) Patent No.: US 10,433,636 B2
(45) Date of Patent: Oct. 8, 2019

(54) PERSONAL HYGIENE DEVICE HAVING TREATMENT-FORCE-MEASUREMENT UNIT

(71) Applicant: Braun GmbH, Kronberg (DE)

(72) Inventors: Jannik Scheele, Kelkheim (DE); Martin Haas, Steinbach (DE); Norbert Schaefer, Frankfurt (DE); Robert Schäfer, Frankfurt (DE); Sven Alexander Franke, Darmstadt (DE); Uwe Schober, Glashuetten-Schlossborn (DE); Ingo Vetter, Karben (DE); Frank Ziegler, Karben (DE)

(73) Assignee: BRAUN GMBH, Kronberg (DE)

( * ) Notice: Subject to any disclaimer, the term of this patent is extended or adjusted under 35 U.S.C. 154(b) by 502 days.

(21) Appl. No.: 15/153,708

(22) Filed: May 12, 2016

(65) Prior Publication Data
US 2016/0331120 A1    Nov. 17, 2016

(30) Foreign Application Priority Data

May 12, 2015    (EP) ..................... 15167364

(51) Int. Cl.
*A46B 15/00*    (2006.01)
*A61C 17/22*    (2006.01)
(Continued)

(52) U.S. Cl.
CPC .......... *A46B 15/0012* (2013.01); *A46B 5/007* (2013.01); *A46B 5/0025* (2013.01);
(Continued)

(58) Field of Classification Search
CPC . A61C 17/221; A46B 15/0012; A46B 5/0025; A46B 15/0014; A46B 15/0044;
(Continued)

(56) References Cited

U.S. PATENT DOCUMENTS 3,986,037 A * 10/1976 Faulhaber ............ G01B 11/105
                                                       250/559.2
4,495,819 A *  1/1985 Tekippe ................. G01L 11/02
                                                       250/231.19
(Continued)

FOREIGN PATENT DOCUMENTS

DE        3414623        10/1985
EP        0339983 A2     11/1989
(Continued)

OTHER PUBLICATIONS

Paul P L Regtien: "Force, Torque and 1-15 Strain Sensing" In: "Sensors for Mechanotronics", Oct. 1, 2012 (Oct. 1, 2012), Elsevier, St. Louis, MO, USA, XP055218855, pp. 211-213, * figure 7.39(A).

(Continued)

*Primary Examiner* — Shay Karls
(74) *Attorney, Agent, or Firm* — Vladimir Vitenberg (57) ABSTRACT

A personal hygiene device has a handle, a treatment head mounted for relative movement of at least a portion thereof with respect to the handle against a restoring force when a treatment force is applied in at least one direction onto the treatment head, a treatment-force-measurement unit for determining the applied treatment force comprising a light-emitting element, a light-sensitive element, and a light-changing element arranged at least partly in the light path between the light-emitting element and the light-sensitive element, wherein the light-changing element and at least one of the light-emitting element and light-sensitive element are arranged to be moved relatively to each other when at least the portion of the treatment head is moved.

15 Claims, 3 Drawing Sheets

(51) Int. Cl.
  *A46B 5/00* (2006.01)
  *A46B 9/04* (2006.01)
(52) U.S. Cl.
  CPC .............. *A46B 9/04* (2013.01); *A46B 15/004* (2013.01); *A46B 15/0014* (2013.01); *A46B 15/0034* (2013.01); *A46B 15/0044* (2013.01); *A46B 15/0046* (2013.01); *A61C 17/221* (2013.01)
(58) Field of Classification Search
  CPC . A46B 15/0036; A46B 15/0038; A46B 5/007; A46B 9/04; A46B 15/0034; A46B 15/004; A46B 15/0046
  USPC .......................... 15/105, 22.1; 433/316, 216
  See application file for complete search history.

(56) References Cited

U.S. PATENT DOCUMENTS

| | | | | | |
|---|---|---|---|---|---|
| 4,698,869 | A | * | 10/1987 | Mierau | A46B 15/0002 15/105 |
| 4,962,328 | A | * | 10/1990 | Woss | H03F 1/303 327/540 |
| 5,054,154 | A | * | 10/1991 | Schiffer | A46B 5/0062 15/143.1 |
| 5,493,747 | A | * | 2/1996 | Inakagata | A61C 17/3418 15/22.1 |
| 5,690,486 | A | * | 11/1997 | Zigelbaum | A61C 19/10 356/405 |
| 6,073,262 | A | * | 6/2000 | Larkin | G05B 9/03 714/736 |
| 6,690,505 | B1 | * | 2/2004 | Ye | H01S 3/1301 359/337 |
| 7,281,289 | B1 | * | 10/2007 | Mirza | A46B 5/0075 15/144.1 |
| 7,453,986 | B1 | * | 11/2008 | Isaksen | A61B 6/145 378/38 |
| 8,544,131 | B2 | | 10/2013 | Braun et al. | |
| 9,549,841 | B2 | * | 1/2017 | Hermanson | A61F 5/566 |
| 2004/0134924 | A1 | * | 7/2004 | Hansen | A47K 10/36 221/9 |
| 2005/0151975 | A1 | * | 7/2005 | Melnyk | G01B 11/18 356/480 |
| 2005/0157305 | A1 | * | 7/2005 | Yu | G01D 5/35303 356/480 |
| 2010/0245840 | A1 | * | 9/2010 | Vernooy | G01L 9/0079 356/519 |
| 2010/0310207 | A1 | * | 12/2010 | Kurtz | G01L 9/0079 385/13 |
| 2010/0325828 | A1 | | 12/2010 | Braun et al. | |
| 2011/0010875 | A1 | * | 1/2011 | Iwahori | A46B 15/0006 15/22.1 |
| 2011/0071436 | A1 | * | 3/2011 | Althoefer | A61B 5/103 600/587 |
| 2011/0314677 | A1 | * | 12/2011 | Meier | A46B 5/0062 30/41.8 |
| 2012/0050735 | A1 | * | 3/2012 | Higgins | G01L 1/24 356/326 |
| 2014/0072930 | A1 | * | 3/2014 | Pruckner | G01J 5/041 433/27 |
| 2014/0278185 | A1 | * | 9/2014 | Landmann | G01K 15/005 702/98 |
| 2014/0310900 | A1 | * | 10/2014 | Curry | A46B 9/04 15/167.1 |
| 2016/0331120 | A1 | * | 11/2016 | Scheele | A46B 15/0012 |

FOREIGN PATENT DOCUMENTS

| | | | |
|---|---|---|---|
| JP | S50105335 | 8/1975 | |
| JP | H814943 | 1/1996 | |
| JP | 2000310509 | 11/2000 | |
| JP | 2006337134 | 12/2006 | |
| SU | 1508091 A1 | 9/1989 | |
| WO | WO 2014098950 A1 * | 6/2014 | ......... A46B 15/0012 |

OTHER PUBLICATIONS

International Search Report with written opinion, dated Jul. 12, 2016, 11 pages.

* cited by examiner

PERSONAL HYGIENE DEVICE HAVING TREATMENT-FORCE-MEASUREMENT UNIT

FIELD OF THE INVENTION

The present invention is concerned with a personal-hygiene device, such as, e.g., a toothbrush, having a treatment-force-measurement unit, in particular wherein the treatment-force-measurement unit is arranged to measure the treatment force applied at a treatment head that is mounted for movement under application of a treatment force relative to a handle of the device.

BACKGROUND OF THE INVENTION

It is known that a toothbrush can be equipped with a treatment-force-measurement unit for determining when a treatment force with which a toothbrush head is pushed against the teeth reaches a predetermined treatment-force threshold value. Such a treatment-force-measurement unit may comprise a strain gauge sensor. It is also known that reaching the pre-determined treatment-force threshold value can be visually indicated. DE 34 146 23 C1 generally discusses such a toothbrush. The present disclosure provides a personal hygiene device having a novel treatment-force-measurement unit.

SUMMARY OF THE INVENTION

In one aspect, there is provided a personal hygiene device having a handle, a treatment head mounted for relative movement of at least a portion of the treatment head with respect to the handle against a restoring force when a treatment force is applied in at least one direction onto the treatment head, a treatment-force-measurement unit for determining the applied treatment force comprising a light-emitting element, a light-sensitive element, and a light-changing element arranged at least partly in the light path between the light-emitting element and the light-sensitive element, wherein the light-changing element and at least one of the light-emitting element or light-sensitive element are arranged to be moved relatively to each other when at least the portion of the treatment head is moved.

BRIEF DESCRIPTION OF THE DRAWINGS

The present disclosure will be further elucidated by a detailed description of several exemplary embodiments shown in figures.

DETAILED DESCRIPTION OF THE INVENTION

In the present disclosure, reference is mainly made to a personal hygiene device comprising an electric toothbrush. This shall not exclude other personal hygiene devices—also contemplated by this disclosure—such as, e.g., manual toothbrushes, safety razors, electric shavers, massage devices, epilators, etc., which devices can benefit in various ways from a determination of a treatment force applied at a treatment head, in particular by indicating a correct range of the applied treatment force for achieving good treatment results.

The term "light" shall mean any suitable electromagnetic radiation, in particular light in the wavelength range typically visible to the human eye (which in the present application shall mean the wavelength range between 400 nanometer (nm) and 700 nm), in the infrared wavelength range (which in the present application shall mean the wavelength range between 700 nm and 1 millimeter (mm)) or in the ultraviolet wavelength range (which in the present application shall mean the wavelength range between 10 nm and 400 nm). In some embodiments, light that is essentially invisible for the human eye is used so that the user of the proposed personal hygiene device is not distracted or confused by visible light that may shine through the handle of the personal hygiene device.

A "light-emitting element" may be any suitable element such as a light emitting diode (LED), an organic LED (OLED), a laser or laser diode, or a regular lamp (arc lamp, gas discharge lamp etc.). In case of an LED, an infrared LED may be used, e.g., an LED based on gallium arsenide that may have an emission wavelength of 840 nm, 850 nm, 875 nm, 880 nm, 885 nm, 890 nm, 940 nm, or 950 nm LEDs based on gallium nitride may be used for emitting ultraviolet light, in particular in the near UV wavelength range of between 375 nm to 395 nm UV LEDs down to a wavelength of 240 nm are commercially available and are considered as well. LEDs emitting light in the visible wavelength ranges (e.g., blue, red, or green LEDs) may be used as well a bi-color, tri-color, or RGB-LEDs.

A "light-sensitive element" may in particular be realized as a photodiode, in particular as silicon (Si) or germanium (Ge) based photodiode. Si-based photodiodes have high responsiveness in particular in the higher IR wavelength range (e.g., around 940 nm). Phototransistors, CCD- or CMOS-based light sensors, photoresistors, photoconductors etc. may also be used as light-sensitive elements. Generally any element that changes its response, in particular its electric characteristic, in dependency on changing light intensity may be usable as light-sensitive element. A light-sensitive element may have a finite light sensitive area (e.g., the light sensitive area may be 1 $mm^2$, even though this value shall not be construed as limiting).

A "light-changing element" is an element that interacts with the light that is emitted by the light-emitting element and progresses along a light path to eventually impinge onto the light-sensitive element of the light-sensitive element. "Interaction" shall here include absorption as well as reflection and scattering. In embodiments with a light-changing element that interacts with the light by means of absorption, a direct light path exists between light-emitting element and light-sensitive element and a relative movement of the light-changing element shall lead to a change in the amount of absorbed light so that an output signal of the light-sensitive element changes accordingly. The light-changing element may in particular be designed such that a relative movement of the light-changing element out of a rest position up to a maximally deflected position leads in a monotone manner (i.e. without flat areas) from a minimum light absorption (i.e. maximum output signal of the light-sensitive element) to a maximum light absorption (i.e. minimum output signal of the light-sensitive element) or vice versa, so that an unambiguous relationship between movement of the treatment head (and thus applied treatment force) and output signal of the light-sensitive element is achieved. Any such shape fulfilling such a monotone light absorption shall be understood as a gray wedge. Then each output signal can be related (in particular via calibration) to an applied treatment force acting on the treatment head. In some embodiments, the relationship between the output signal of the light-sensitive element and the applied treatment force is calibrated, e.g., at the plant of the manufacturer, i.e. the treatment-force-measurement unit is than arranged for calibration.

Similarly, in embodiments with a light-changing element that interacts with the light by means of reflection (e.g., the light-changing element may be realized as a mirror), an indirect light path exists between light-emitting element and light-sensitive element, i.e. the light that impinges on the light-sensitive element has previously been reflected by the light-changing element. Relative movement of the light-changing element shall lead to a change in the amount of light impinging onto the light-sensitive element and the overall unit may again be designed as mentioned before to achieve an unambiguous relationship between movement of the treatment head and output signal of the light-sensitive element. The above shall not exclude embodiments in which both, a light-absorbing element and a light-reflecting element are utilized.

In embodiments with a light-absorbing element, it is to be differentiated between (a) light attenuation due to changing thickness (or material composition) of the light-absorbing element leading to changes in the intensity of the light impinging onto the light sensitive detector and (b) light attenuation due to a change in a light shadowing area (i.e. the light-changing element may be translucent or opaque for the emitted light but the coverage of the light-sensitive element by the opaque light-changing element changes under application of a treatment force at the treatment head). The first type of embodiments is based on a light-changing element that is designed so that the light is only partly absorbed (or scattered away, even though materials with a high absorption to scattering ratio lead to less issues with scattered light eventually impinging onto the light-sensitive element) when it passes through the light-changing element. The light-changing element may completely cover the sensitive area of the light-sensitive element and essentially only changes in the thickness or material composition will then lead to a change in light intensity on the light sensitive detector. The light-changing element may then be made from a material or materials that are translucent for the used light wavelength. The light-changing element may then have a thickness that is monotonically (i.e. without flat areas) increasing from a lower (or higher) thickness to a higher (or lower) thickness in the movement direction. Such a type of light attenuating element is named a "gray wedge" in accordance with the present description. The latter type of embodiments (i.e. embodiments including light shadowing) is based on a light-changing element that is only partly covering the area of the light-sensitive element. The light-changing element may then be translucent or opaque. In some embodiments, aspects of light attenuation and of light shadowing are combined.

With the term "restoring force", resilient, i.e. spring-like forces are meant that act against the treatment force. The restoring force may be realized by a resilient element, e.g., a spring element and then the restoring force essentially has a linear behavior at least for the relevant deflection range, while it shall not be excluded that the restoring force may have a non-linear behavior. In such embodiments, the treatment head may be pivotably connected with the handle; e.g., a hinge may be provided for movement of the treatment head around a pivot axis relative to the handle. In some embodiments, application of the treatment force at the treatment head elastically deforms essentially only a portion of the treatment head (such that only a portion of the treatment head is deflected with respect to the handle) and the elastically deformed portion provides the restoring force acting against the treatment force. Such a restoring force may have a non-linear behavior despite providing a monotone increase of the restoring force acting against the deformation with increased applied treatment force.

In some embodiments, at least one light-absorbing surface is arranged in proximity of the light path. A light-absorbing surface serves to absorb light that is, e.g., scattered away by the light-changing element instead of being absorbed. The light-absorbing surface also serves to absorb light that is emitted by the light-emitting element at large angles. Otherwise, scattered light or light emitted at large angles may be reflected by the surfaces surrounding the light path and the reflected light may eventually impinge onto the light-sensitive element and may thus distort the light intensity measurement. A light-absorbing surface in accordance with the present disclosure may be realized by blackening a surface (e.g., by applying a black and matt color to the surface) or by lining the surfaces in the proximity of the light path with light absorbing material such as a light absorbing foil or by enclosing the light path area in a light absorbing sheath or cover.

The movement of the treatment head relative to the handle under application of a treatment force may depend on temperature. In particular in embodiments in which no hinge is provided for the movement of the treatment head relative to the handle, but where the elasticity of a portion of the treatment head is used to achieve the relative movement, the elasticity modulus of the material of said portion of the treatment head is depending on the temperature. But also in other embodiments, a temperature dependency may be present as due to temperature changes certain geometric relations may shift (e.g., due to thermal expansion) or the response of the light-sensitive element may change. In order to compensate for temperature-depending effects, the personal hygiene device may comprise a temperature sensor and a temperature-compensation circuit. The temperature sensor may then be arranged to provide a signal indicative of the ambient temperature and the temperature-compensation circuit may then be arranged to compensate the temperature dependency from the output signal of the light-sensitive element. The temperature dependency may be measured at the manufacturer's plant for each device and the respective compensation factors to be employed by the temperature-compensation circuit are then individualized. In other embodiments, the general temperature dependency may be determined based on a certain amount of device samples and universal compensation factors may then be employed.

In some embodiments, the personal hygiene device comprises a drift-compensation circuit to correct for a signal drift over time due to e.g., aging of the components. The drift-compensation circuit in particular determines the output signal of the light-sensitive element for zero applied treatment force (zero load).

Figure 1:
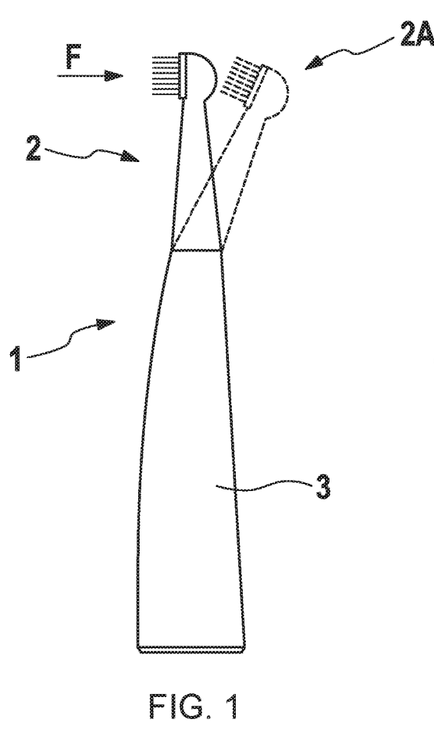
FIG. 1 is a depiction of an exemplary personal hygiene device comprising an electric toothbrush.
Figure 1A:
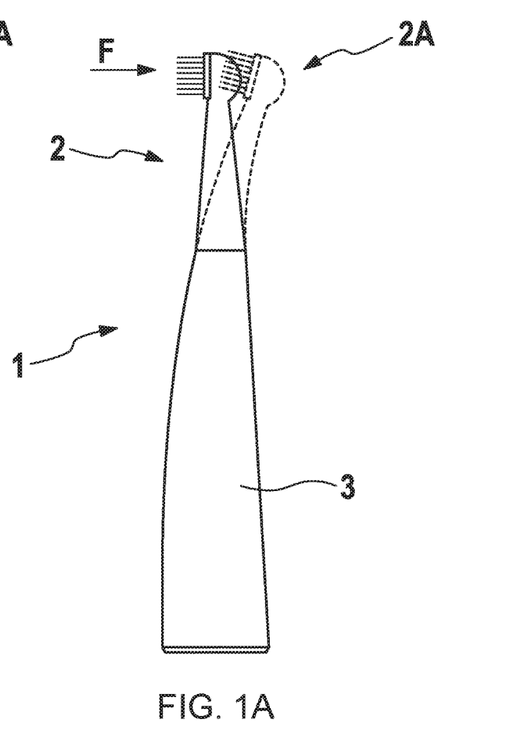
FIG. 1A is a depiction of an exemplary personal hygiene device comprising an electric toothbrush and experiencing elastic deformation.

FIG. 1 is a depiction of an exemplary personal hygiene device 1, here realized as an electric toothbrush. The personal hygiene device 1 has a treatment head 2 that is mounted at a handle 3 so that a treatment force F acting onto the treatment head 2 in at least one direction leads to a movement of the treatment head 2 relative to the handle 3 (indicated by a deflected treatment head 2A shown in dashed lines, where the deflection is exaggerated for sake of visualization). As will be explained in more detail below, the personal hygiene device 1 has a treatment-force-measurement unit that is arranged to measure a light intensity that is indicative of the movement of the treatment head 2 relative to the handle 3 under application of the treatment force F, where the relationship between the applied treatment force F and the light intensity is known or at least can be calibrated. The movement of the treatment head 2 relative to the handle 3 may be a movement around a pivot point or pivot axis, may be an elastic deflection or any other type of relative movement. A spring force acting against the movement or deflection may be provided by a resilient element (e.g., a spring) arranged between the treatment head and the handle or the spring force may be generated due to an elastic deformation of a portion of the treatment head 2.

Figure 2:
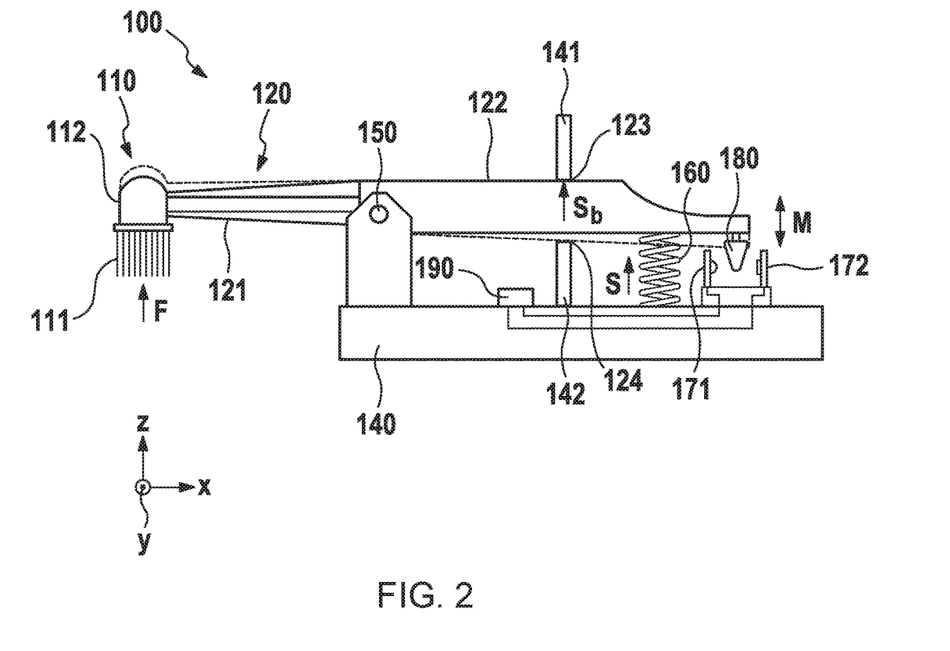
FIG. 2 is a schematic depiction of an exemplary embodiment of the personal hygiene device having a treatment-force-measurement unit.

FIG. 2 is a schematic simplified depiction of a personal hygiene device 100 comprising a treatment head 120 that is pivotably mounted at a handle 140 (here for sake of simplicity just indicated by a wall element). A coordinate system having x-, y-, and z-axis is shown as reference (the y-axis extends into the paper plane). The treatment head 120 is arranged to be moveable around a pivot axis 150 (here extending in y direction) against a spring force S provided by a resilient element 160 (which may have a linear spring constant at least in the range of forces that typically occur in a treatment session—i.e. treatment forces in the range of between about 0.5 Newton and about 7 Newton) arranged between the handle 140 and the treatment head 120. Provision of a pivot axis shall be considered as non-limiting and other linkages between treatment head and handle are considered as well. A treatment force F being applied at the treatment head 120 will cause such a deflection (here, the treatment force is applied at a front portion 110 of the treatment head 120). In order to move the treatment head 120 around the pivot axis 150, the applied treatment force F needs to have at least one force component that acts as a torque (i.e. moment of force) around the pivot axis 150. With reference to the coordinate system, the treatment force F must initially have a component in the z direction; generally, the treatment force F must have a component that lies in a plane to which the pivot axis 150 is normal and which component is perpendicular to a radial line originating at the pivot axis and extending in said plane. Thus, the term "treatment force" in the present disclosure shall mean a force that has such a force component that can turn the treatment head 120 around the pivot axis 150 and all force values given herein, if not stated otherwise, relate to this force component. The personal hygiene device 100 generally extends in a longitudinal direction (here the x direction) between a first end (front portion 110 of the treatment head 120) and a second end (back end 149 of the handle 140).

The front portion 110 of the treatment head 120 is here indicated as a brush head for use with an electric toothbrush. The front portion 110 has here a carrier element 112 (which may be mounted for movement relative to the treatment head 120) on which treatment elements 111 (here: cleaning elements such as tufts made from nylon filaments or elastomeric cleaning fingers etc.) are mounted.

The treatment head 120 may have a front arm 121 that extends from the pivot axis 150 to the front portion 110 and an arm element 122 that extends from the pivot axis 150 towards the back end of the handle 140. In the shown embodiment, the arm element 122 tapers towards its back end; this shall be understood as just a non-limiting design option). A resilient element 160 (here indicated as a mechanical coil spring) is arranged between the handle 140 and the treatment head 120, here between handle 140 and arm element 122 of the treatment head 120. In some embodiments, a first stopper 141 that is fixedly mounted with respect to the handle 140 is arranged so that a rest position of the treatment head 120 is defined when no treatment force F is applied. In the rest position, the treatment head 120 abuts the first stopper 141 at abutment point 123. The rest position may be mechanically calibrated in a manner so that no biasing spring force $S_b$ acts against the treatment head 120. In some embodiments, the rest position may be defined such that a biasing spring force $S_b \neq 0$ Newton (N) acts against the treatment head 120 towards the first stopper 141 so that only an applied treatment force F that overcomes this biasing spring force $S_b$ ($F > S_b$) will move the treatment head 120 away from the first stopper 141 around the pivot axis 150. The biasing spring force $S_b$ may be set such that a treatment force F between 0.5 N and 2 N starts to move the treatment head 120. The biasing spring force $S_b$ may in particular be set such that a treatment force F of at least 0.5 N, 0.75 N, 1.0 N, 1.25 N, 1.5 N, 1.75 N, or 2.0 N starts to move the treatment head 120.

The shown embodiment shall not exclude that at least a front portion of the treatment head is arranged to be repeatedly detachable from the handle and that at least a portion of the arm element 122 is non-detachably connected with the handle. The arm element 122 may then become connected with the treatment head 120 once it become attached to the handle 140 and then moves when the applied treatment force F deflects the treatment head 120.

In some embodiments, a second stopper 142 is mounted fixedly with respect to the handle 140 and defines a maximum deflection position of the treatment head 120. As indicated by dashed lines, the maximally deflected treatment head 120 abuts the second stopper 142 at abutment point 124. The first stopper 141 and the second stopper 142 define a maximum deflection range around the pivot axis 150 out of the rest position. The maximum deflection position provided by the second stopper 142 may be calibrated to relate to an applied treatment force in the range of between 2.5 N to 7.5 N and may in particular be set to 2.5 N, 3.0 N, 3.5 N, 4.0 N, 4.5 N, 5.0 N, 5.5 N, 6.0 N, 6.5 N, 7.0 N, or 7.5 N.

The personal hygiene device 100 further comprises a treatment-force-measurement unit that includes a light-emitting element 171, a light-sensitive element 172, and a light-changing element 180 arranged in a light path between the light-emitting element 171 and the light-sensitive element 172. The light-changing element 180 is here shown as a light-absorbing element. Alternatively or additionally, the light-changing element 180 may be realized as a light-reflecting element. When a treatment force F is applied at the treatment head 120 so that the treatment head is deflected, the arm element 122 moves as a result of the relative movement of treatment head 120 and handle 140 and the relative position of the light-changing element 180 with respect to at least one of the light-emitting element 171 and the light-sensitive element 172 is changed so that the light intensity measured by the light-sensitive element 172 is changed (as indicated by double arrow M). Thus the light intensity measured by the light-sensitive element 172 is a parameter indicative of the value of the applied treatment force F. As will be described below, a signal value provided by the light-sensitive element 172 can be calibrated so that a precise absolute value of the applied treatment force F can be determined. The maximum deflection of the elements of the treatment-force-measurement unit relatively to each other is the movement length. The length extension of the light-changing element along the direction of the movement is in some embodiments longer than the movement length, in particular in some embodiments where the light-changing element is realized as a translucent gray wedge.

In some embodiments, a SMD mountable phototransistor was used as light-sensitive element, e.g., an Everlight PT12-21B/TR8 (EVERLIGHT ELECTRONICS CO., LTD., Taipei, Taiwan), which has a bandwidth of 400 nm to 1100 nm and peak sensitivity at 940 nm. In some embodiments, a SMD mountable LED was used as light-emitting element, e.g., an Everlight Right Angle Lens IR-12-21C/TR8, which has a peak wavelength at 940 nm and a spectral bandwidth of 45 nm. In some embodiments, an Osram SFH 4045N LED having a peak wavelength of 950 nm was utilized. The Osram SFH 4045N LED has a small emission cone having a half angle of ±9 degrees. A confined and small emission cone tends to generation of less background noise. Background noise may be generated by light emitted at large angles, which light may eventually impinge onto the light-sensitive element after having been reflected. In some embodiments an Everlight IR26-51C-L110 LED having a peak wavelength of 940 nm and a view angle of 20 degrees (i.e. a half angle of ±10 degrees) was used.

In some embodiments, the light-changing element was made from polypropylene (PP) HW11L. In some embodiments, the light-changing element was made from polyoxymethylene (POM) Hostaform C9021 (available from Celanese GmbH, Sulzbach am Taunus, Germany) Depending on the pigments added to these materials, typical 1/e lengths' (i.e. the length of material after which a light beam had been attenuated by 1/e (around 37%)) had been measured for these materials that were in the range of between 1 mm to 4 mm for the used light (IR radiation having a wavelength of 950 nm). It had been found that an attenuation of around 1/e to about 50% between the extreme deflection positions provides good overall sensor performance (to some extent, the performance also depends on the series resistor used to drive the photodiode—series resistors with a resistance in between 150 Ohm to 250 Ohm were used in particular for the before mentioned LEDs—and/or the pull-up resistor used to drive the phototransistor—pull-up resistors with resistance values in between 500 Ohm and 1500 Ohm were used in particular for the before mentioned phototransistor). Thus, in some embodiments, the light-changing element was designed such that the attenuation between the extreme states of deflection was in a range of between about 1/e (about 37%) to about 50%. POM Hostaform C9021 white had been measured to have an attenuation coefficient of about 0.9 mm$^{-1}$ (for IR radiation having a wavelength of 950 nm), which allowed relatively small sized light-changing elements suitable for personal hygiene devices.

Figure 3:
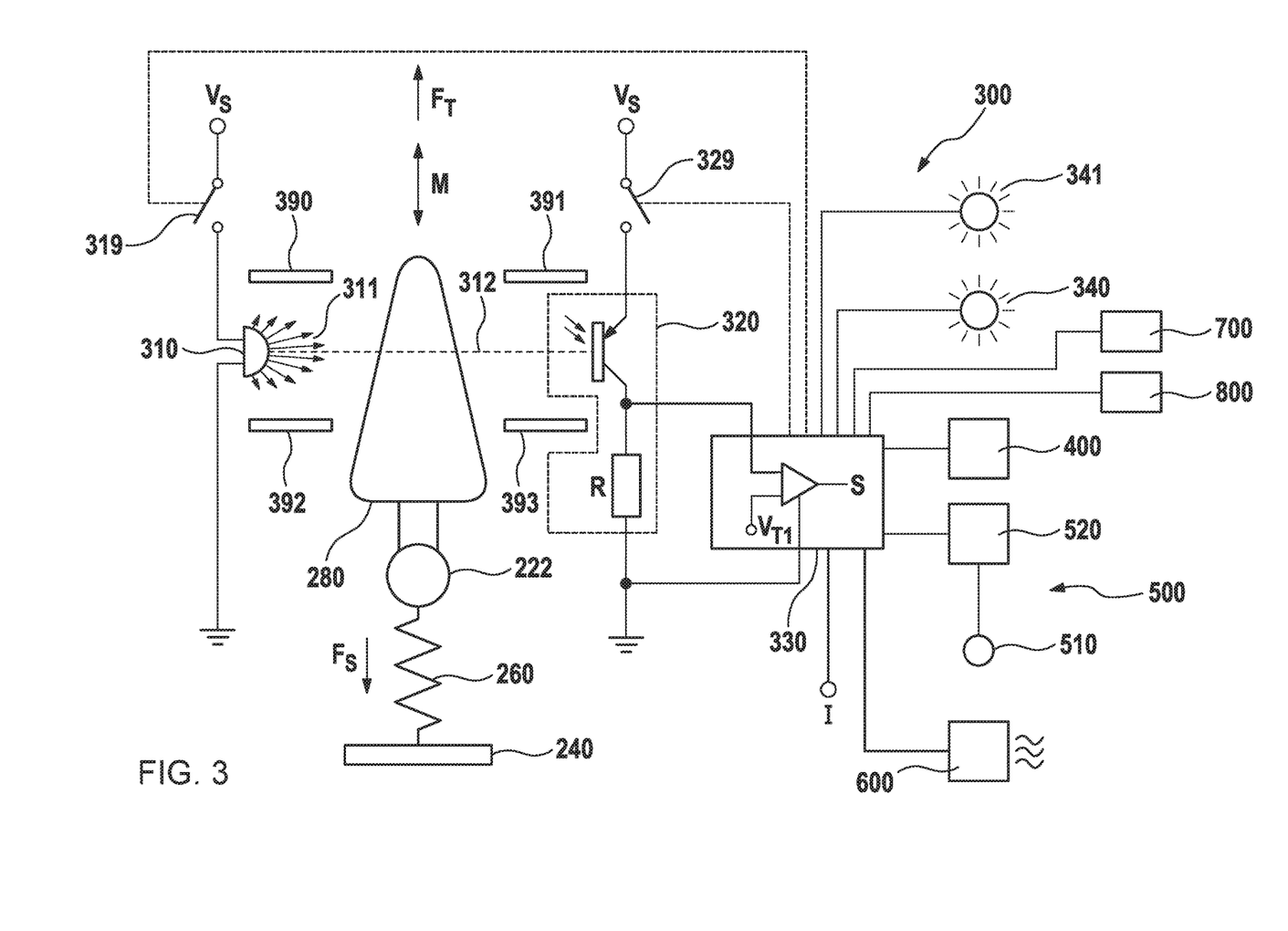
FIG. 3 is a schematic depiction of various components of an exemplary treatment-force-measurement unit.

FIG. 3 is a schematic and simplified depiction of various components of a personal hygiene device in accordance with the present disclosure including an exemplary treatment-force-measurement unit 300 comprising a light-emitting element 310 (which may be realized as an IR LED), a light-sensitive element 320 (which may be realized as a phototransistor), a control circuit 330, and a light-changing element 280, which is here without limitation shown as a gray wedge, which may in particular be realized as a translucent gray wedge, and in particular as a translucent gray wedge that always covers the sensitive area of the light-sensitive element with respect to the light emitted by the light-emitting element. In an active state, the light-emitting element 310 and the light-sensitive element 320 are powered by an energy supply (e.g., comprising a battery or an accumulator) providing a source voltage $V_S$.

As has been explained before, the light-changing element 280 that is here secured at a moving portion 222 of a treatment head is moved under application of a treatment force $F_T$ against the restoring force $F_S$ of a resilient element 260 (here realized as a mechanical coil spring) along a movement direction indicated by double arrow M (as mentioned before, also other elements of the treatment-force-measurement unit may additionally or alternatively be arranged to be movable). The maximum deflection along movement direction is considered to be the movement length. The resilient element 260 is on one end secured with respect to a housing 240 of the personal hygiene device and on the other end it is secured with respect to the moving portion 222 (e.g., an arm element 122 as discussed with respect to FIG. 2). The light-emitting element 310 has here a directional characteristic 311 with an intensity peak in the center (indicated by differently long arrows) so that light is essentially emitted along a light path 312 directed towards a center of a sensitive area of the light-sensitive element 320. Light-absorbing surfaces 390-393 are schematically indicated, which may be arranged in proximity of the light path 312 so that light that is e.g., emitted at large angles from the light-emitting element 310 or light that is scattered away by the light-changing element 280 is absorbed. Otherwise scattered light or light emitted at large angles may become reflected by non-absorbing surfaces and may then eventually impinge onto the sensitive area of the light-sensitive element 320, which would distort the light intensity measurement. It is noted that the number and position of the light-absorbing surfaces is within the discretion of the designer. In some embodiments, only a single light-absorbing surface may be present, in other embodiments, several light-absorbing surfaces are utilized. In the shown embodiment, light impinging onto the active light-sensitive element 320 leads to a light-intensity depending current flow through a resistor R, which changing current flow then leads to a change in the voltage over the resistor R. The voltage over the resistor R is measured by the control circuit 330.

The control circuit 330 has an input I via whom the control circuit 330 may receive a signal when the personal hygiene device is switched on. The control circuit 330 may then activate the light-emitting element 310 and the light-sensitive element 320 by switching on respective switches 319 and 329. The control circuit 330 may compare the voltage over the resistor R with at least a first pre-determined threshold voltage $V_{T1}$, so that based on this comparison, a signal S indicates whether the measured voltage is above or below the first pre-determined threshold voltage $V_{T1}$. The first pre-determined threshold voltage $V_{T1}$ may be calibrated such that it relates to a first pre-determined treatment force value of, e.g., 1.5 N or 2 N as discussed before. Based on the comparison result (i.e. based on the signal S), the control circuit 330 can control at least a first indication element 340 to provide a user noticeable signal (e.g., a visual signal, an audible signal, or a tactile signal). The first indication element 340 may thus be realized as a light emission element such as an LED, as a loudspeaker, or as a vibrator, e.g., a piezo-vibrator. The first indication element 340 can then be activated as long as the applied treatment force $F_T$ has a value that is below (or above) a first pre-determined treatment force value. At least a second pre-determined threshold voltage may be provided (which may, e.g., be calibrated to a second pre-determined treatment force value of, e.g., 3 N) and the control circuit 330 can then indicate via the first indication element 340 that the applied treatment force $F_T$ is between the first and the second pre-determined treatment force values. At least a second indication element 341 may be provided to indicate, e.g., that the applied treatment force $F_T$ is above the second pre-determined treatment force value. The second indication element 341 may be realized as one from the list of realization possibilities given above for the first indication element. In some embodiments, the first indication element 340 may be realized as a green LED, while the second indication element 342 may be realized as a red LED. In some embodiments, the control circuit 330 is calibrated so that the absolute value of signal S relates to a treatment force value and the precise application of treatment forces over time can be monitored and analyzed.

In some embodiments, the control circuit 330 comprises a drift-compensation circuit 400 for determining a reference voltage representing zero applied treatment force, in particular wherein the drift-compensation circuit is arranged to apply a median value determination based on voltage signals prior to an instant when the personal hygiene device is switched on. In some embodiments, the control circuit 330 comprises a temperature correction unit 500 comprising a temperature sensor 510 and a temperature correction circuit 520. The temperature correction circuit 520 may be arranged to correct the voltage value measured by the control circuit 330 for temperature depending effects. Further, in some embodiments the personal hygiene device comprises a transmitter unit 600 for establishing at least a one-directional wireless connection with an external device, e.g., for communicating data from the personal hygiene device to the external device, in particular for the purpose of analyzing and/or displaying information about the treatment session to the user. FIG. 3 also indicates that in some embodiments additional components may be present such as, e.g., an automatic adjustment circuit 700 and/or a user input unit 800. These aspects will be further described in below paragraphs "Consumer adjustment of pre-determined treatment-force threshold value" and "Automatic adjustment of the pre-determined threshold".

Drift Compensation

As mentioned before, the personal hygiene device may have a drift-compensation circuit for correcting a drift in the output signal of the light-sensitive element over time, e.g., due to aging. In particular, the drift-compensation circuit determines the output signal of the light-sensitive element for zero applied treatment force. One possible realization of such a drift-compensation circuit is described in the following: the drift-compensation circuit reads the output signal from the activated light-sensitive element during a given time period (which may happen, e.g., once every month, even though this shall not exclude that the drift-compensation circuit stores output signal values always while the personal hygiene device is switched off) and writes the output signals into an internal memory. The drift-compensation circuit may thus be arranged to wake the treatment-force-measurement unit. Once the personal hygiene device is switched on, the drift-compensation circuit stops storing output signals to not falsify the measurement due to forces being applied at the treatment head. If not enough output signal values were stored up the instant the personal hygiene device was eventually switched on, the drift-compensation circuit may be arranged to repeat the procedure, e.g., 6 hours later. The drift-compensation circuit may be arranged to read output signal values from the light-sensitive element at a frequency in the range of between about 0.5 Hz to 5 Hz, even though these values are not to be construed as limiting. The drift-compensation circuit may store the output signal values into the memory for a period of between about 1 second to about 600 seconds. As it cannot be ensured that the user does not use the personal hygiene device prior to switching it on (e.g., a user of a toothbrush may hold the brush head under water prior to applying toothpaste, which are both acts during which a force is applied at the treatment head leading to a respective change of the output signal of the light-sensitive element), the drift-compensation circuit may apply a median filtering by which extreme output signal values are filtered out. The computed median value was found to be reliable with a error in the range of 0.044 N for a sample rate of 1 Hz and a data collection of 10 output signal values during which the toothbrush was used prior to switching it on. In some embodiments, the personal hygiene device comprises an acceleration sensor and output signal values are not stored while the toothbrush is moved. The thus computed zero treatment force output signal value is then used by the treatment-force-measurement unit for zero treatment force calibrated measurements until a new value is provided by the drift-compensation circuit. In some embodiments, the personal hygiene device is arranged to detect whether it is placed on a holder (e.g., a charger), under which circumstances the drift-compensation circuit may be arranged to wake the treatment-force-measurement unit to record output signals from the light-sensitive element as it should be a reliable assumption that no force is applied at the treatment head while the personal hygiene device is placed on the holder.

Calibration

It is contemplated that the personal hygiene device as disclosed herein may be calibrated, e.g., at the plant of the manufacturer. A series of at least two or more precisely controlled load values may be applied at the treatment head so that the treatment-force-measurement unit can calibrate the signals from the light-sensitive element versus the applied force values. The personal hygiene device may be provided with a particular calibration mode in which the respective force values to be applied during calibration are pre-programmed and the parameter values which are measured during the calibration procedure are then used for a respective calibration. In an alternative or additional embodiment, the personal hygiene device can communicate with an external device (a wired or wireless connection may be used) via which the applied load values are communicated from the external device to the personal hygiene device for using these values in the calibration. Alternatively or additionally, the signals from the light-sensitive element may be communicated from the personal hygiene device to the external device, which then performs the calibration and communicates back calibration parameters to be applied. In the latter embodiment, a complex calibration circuit is not necessary in the personal hygiene device.

Consumer Adjustment of Pre-Determined Treatment-Force Threshold Value

The personal hygiene device may be equipped with a user input unit for adjusting at least one of the pre-determined treatment-force threshold values (or for adjusting the pre-determined treatment-force threshold value if only one such value is set). Such a user input unit may be realized as a simple switch or as a touch-sensitive pad. In some embodiments, the user input unit is realized as a wireless connectable receiver or transceiver for receiving (and optionally transmitting) data between an external device (e.g., a smartphone onto which a suitable application was loaded) and the personal hygiene device. In the latter embodiment, comfortable and manifold setting possibilities can be realized without the need to realize the respective complex user input unit in the personal hygiene device.

Automatic Adjustment of the Pre-Determined Threshold

Two different possible examples of an automatic adjustment of at least one pre-determined treatment-force threshold value are discussed. In the first example, the personal hygiene device is arranged for an automatic adjustment when a treatment mode of the personal hygiene device is changed. In case of toothbrushes, e.g., it is known to provide different brushing modes such as "Standard Cleaning Mode", "Soft Cleaning Mode", or "Gum Care Mode". While the pre-determined treatment-force threshold value for the applied treatment force may be set to 3 N for the "Standard Cleaning Mode", the pre-determined treatment-force threshold value may be changed to 2.5 N in case the "Soft Cleaning Mode" is chosen or, e.g., to 2.0 N if the "Gum Care Mode" is chosen. Depending on the chosen treatment mode, the device can then indicate a dedicated too high treatment force. In the second example, the personal hygiene device (in particular the treatment-force-measurement unit) is arranged to measure a time series of applied treatment force values and to automatically adjust the pre-determined treatment-force threshold value(s) based on the habits of the user. An automatic adjustment unit may be provided for performing the mentioned automatic adjustments.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal hygiene device, comprising:
   a handle;
   a treatment head mounted for relative movement of at least a portion of the treatment head with respect to the handle against a restoring force when a treatment force is applied in at least one direction onto the treatment head;
   a treatment-force-measurement unit for determining the applied treatment force comprising a light-emitting element, a light-sensitive element, and a light-changing element arranged at least partly in the light path between the light-emitting element and the light-sensitive element;
   wherein the light-changing element and at least one of the light-emitting element and light-sensitive element is arranged to be moved relatively to each other when at least the portion of the treatment head is moved, and wherein the treatment-force-measurement unit comprises a control circuit for determining a parameter indicative of a light intensity measured by the light-sensitive element.

2. The personal hygiene device of claim 1, wherein the light-changing element is a light-absorbing element.

3. The personal hygiene device of claim 2, wherein the light-absorbing element is realized as a translucent gray wedge, wherein the gray wedge is arranged to fully cover the light-sensitive element with respect to the light emitted by the light-emitting element.

4. The personal hygiene device of claim 2, wherein the light-absorbing element is only partly covering the light-sensitive element with respect to the light emitted by the light-emitting element.

5. The personal hygiene device of claim 2, wherein the light-absorbing element has a wedge-like shape and has a length extension along a direction into which the light-absorbing element is moved under application of a treatment force, which length extension is longer than a maximum movement length.

6. The personal hygiene device of claim 1, wherein the light-changing element is a light-reflecting element.

7. The personal hygiene device of claim 1, wherein at least one light-absorbing surface is arranged in proximity of the light path.

8. The personal hygiene device of claim 1, wherein a first stopper is fixedly provided with respect to the handle so that the treatment head abuts against the first stopper when no treatment force is applied at the treatment head.

9. The personal hygiene device of claim 8, wherein the treatment head is spring-biased and is arranged to move away from the first stopper when a treatment force above a first treatment-force threshold value is applied at the treatment head.

10. The personal hygiene device of claim 1, wherein a second stopper is fixedly provided with respect to the handle against so that the treatment head abuts the second stopper when a treatment force having a second treatment-force threshold value is applied at the treatment head.

11. The personal hygiene device of claim 1, wherein the light-emitting element emits light at a wavelength or in a wavelength range essentially not visible to the human eye.

12. The personal hygiene device of claim 11, wherein the light emitted is in the infrared or ultraviolet wavelength ranges.

13. The personal hygiene device of claim 1, wherein the treatment head and the handle are secured to each other or are integral with each other, and only a portion of the treatment head elastically deforms when the treatment force is applied at the treatment head.

14. The personal hygiene device of claim 1, further comprising a drift-compensation circuit for determining a reference output signal of the light-sensitive element representing zero applied treatment force, wherein the drift-compensation circuit is arranged to apply a median value determination based on output signals from the light-sensitive element prior to an instant when the personal hygiene device is switched on.

15. The personal hygiene device of claim 1, further comprising a temperature sensor and a temperature-compensation circuit.

* * * * *